United States Patent [19]

Seals et al.

[11] Patent Number: 5,149,652
[45] Date of Patent: Sep. 22, 1992

[54] FERMENTATION BROTH DEGASSIFICATION

[75] Inventors: Michael T. Seals; Eugene H. Wegner, both of Bartlesville, Okla.

[73] Assignee: Phillips Petroleum Company, Bartlesville, Okla.

[21] Appl. No.: 529,809

[22] Filed: May 29, 1990

Related U.S. Application Data

[62] Division of Ser. No. 181,358, Apr. 14, 1988, Pat. No. 4,952,509.

[51] Int. Cl.$^5$ .......................... C12N 1/34; C12M 1/21
[52] U.S. Cl. .................................... 435/246; 435/255; 435/256; 435/812; 435/813; 435/819; 55/41; 55/52; 261/DIG. 19
[58] Field of Search ............ 435/243, 246, 253.6, 435/812, 813, 819, 254, 255, 256, 313–316; 261/DIG. 19; 55/36, 38, 40–44, 52, 53, 55, 178, 87

[56] References Cited

U.S. PATENT DOCUMENTS

| | | | |
|---|---|---|---|
| 1,838,475 | 12/1931 | Buswell | 435/812 |
| 2,184,195 | 12/1939 | Naucler | 55/178 |
| 2,657,174 | 10/1953 | Stich | 435/313 |
| 3,056,749 | 10/1962 | Griffith | 55/178 |
| 3,984,286 | 10/1976 | Malick | 435/812 |
| 4,085,007 | 4/1978 | Hawkins | 435/812 |
| 4,097,339 | 6/1978 | Marwil | 435/812 |
| 4,373,024 | 2/1983 | Hunt | 435/41 |
| 4,414,329 | 11/1983 | Wegner | 435/255 |
| 4,617,274 | 10/1986 | Wegner | 435/255 |
| 4,670,397 | 6/1987 | Wegner et al. | 435/243 |

FOREIGN PATENT DOCUMENTS

0017268 2/1977 Japan .................................. 55/178

OTHER PUBLICATIONS

Perry'Chemical Engineer's Handbook, Sixth Ed., N.Y., McGraw-Hill, Inc. 1984, pp. 27-5-27-13.
Manual of Methods for General Bacteriology, Washington, D.C., American Society of Microbiology, 1981, pp. 130-140.
Yeast: Characteristics and Identificatin, Cambridge, G.B., Cambridge Univ. Press, 1983, pp. 23-28.

Primary Examiner—Robert J. Warden
Assistant Examiner—William H. Beisner
Attorney, Agent, or Firm—David L. Kinsinger

[57] ABSTRACT

A post-fermentation degassing technique is provided for use in degassing foamed fermentation broths containing cultured microorganisms. Such a broth is charged while pressurized through a nozzle to form a spray suspension in a gaseous spray chamber located in a gravitationally upper part of a degassing vessel. The spray chamber is vented to the atmosphere. The spray suspension is coalesced to form a bulk liquid phase located in a gravitationally lower portion of the degassing vessel whereby the upper surface of such bulk liquid phase forms the bottom surface of such spray chamber. The nozzle is so oriented that the spray suspension it produces is downwardly directed towards the surface of the bulk liquid phase and the layer of foam characteristically foamed thereon. Additionally, a portion of the bulk liquid phase is recycled to the upper part of the vessel through a second nozzle to form a second spray suspension which is coalesced into the bulk liquid phase.

10 Claims, 2 Drawing Sheets

FERMENTATION BROTH DEGASSIFICATION

This application is a division under 37 C.F.R. 1.60 of application Ser. No. 181,358, filed Apr. 14, 1988, now U.S. Pat. No. 4,952,509, issued Aug. 28, 1990.

BACKGROUND

1. Field of the Invention

This invention lies in the field of processes and apparatus for producing degassed fermentation broth.

2. Prior Art

Fermentors which are pressurizable and which are capable of using high air flow are known, as is technology for culturing microorganisms in such a fermentor. A pressurized culture zone with high air flow is desirable because it improves the rate of oxygen transfer between the microorganisms and the aqueous culturing medium, increases the rate of microorganism growth, and increases the density of microorganisms cultured, but it also increases the foam inherently produced, as those skilled in the art appreciate.

The foam causes a significant problem in post-fermentation separation of the fermentation broth liquid phase from the gas phase which is in the form of entrained gas bubbles (foam). This problem is exacerbated when continuous pressurized fermentation procedures are practiced with high air flow.

The foaming inherently occurs during fermentation, especially when conducted under pressure, and high air flow because the air (oxygen) charged into the fermentor becomes admixed with the aqueous culture medium under the action of medium agitation which is characteristically employed to maintain the medium in a uniform state and to promote transfer of oxygen into microorganisms being aerobically cultured. Certain agents present in the culture medium which originate both from the nutrients charged into the culture medium and from the metabolites excreted from the microorganisms being cultured exert significant surfactant activity and thus tend to create and to stabilize foaming.

Defoaming agents are undesirable additives to a fermentation broth when the fermentation product is intended for food use since they contaminate the broth. Also, the level at which such agents would need to be added in the case of a broth containing a relatively high level of total solids (such as exists when pressurized fermentation is practiced) in order to achieve a practical level of defoaming is so great as to cause operating cost problems and final product purity problems (for example, as regards the level of impurities permitted by the U.S. Food and Drug Administration in human food).

Various mechanical defoaming techniques for use in a fermentor are known, such as rotable metal arm arrangements adapted for flailing the surface regions of a foam, centrifuging, and the like. For example, Hunt U.S. Pat. No. 4,373,024 describes a rotable foam breaking apparatus which is mounted in the upper central portion of a fermentor. When this apparatus functions in an operating fermentor, a foamed fermentation broth is drawn up thereinto along a multitude of paths. At or near the path rotational axes, the gas phase tends to be separated from the liquid phase by centrifugal force, and the latter phase is returned to the main mass of the fermentation broth while the former phase is separated and is vented.

Unfortunately, the rate at which any known apparatus is able to separate the gas phase from the liquid phase in a fermentor seems to be generally insufficient to meet the gas separation requirements existing in high pressurize high air flow continuous fermentation so that such apparatus does not solve the post fermentation gas separation problem.

In the prior art, the post fermentation gas separation problem was typically previously solved by removing the gas-filled fermentation broth from the fermentor and passing such into an open holding reservoir for holding until the gas bubbles collapse. However, the rate of foam collapse is slow, the quantity of gas is large, and the stability of foam is variable from one microorganism to another, and from one nutrient medium to another. Hence, such a "natural" foam removal procedure is not practical for most commercial purposes. Gravity separation is accelerated by the addition of defoaming agent, and the use of such agents in such a separation is sometimes practiced.

Control of the composition of solutes present in an aqueous fermentation liquid (so as thereby to minimize the presence of surface active components therein) is difficult to achieve for many reasons. For one thing, the exact composition of many nutrients and of metabolites from many microorganisms is not now known.

The art of microorganism fermentation, particularly under high pressure high air flow conditions, has great need for a new and effective technique for mechanically degassing a foamed fermentation broth.

SUMMARY

An object of the present invention is to provide a new, improved, effective, economical, and reliable process for degassing a previously pressurized, foam-filled fermentation broth containing cultured microorganisms.

Another object is to provide a new, improved, economical, and reliable continuous process for accomplishing sequentially fermentation and degassing of fermentation broths without using any defoaming agents and by using only a single pressurized fermentation zone and a single, separate degassing zone in generally adjacent relationship to said fermentation zone.

Another object is to provide new and improved apparatus for use in degassing heavily foamed broth from a pressurized fermentor.

Another object is to provide new and improved apparatus for continuously making defoamed fermentation broths which apparatus is suitable for use in pressurized fermentation with high gas flow and which can produce a broth containing a high content of cultured microorganisms without the use of any defoaming agents.

Other and further objects, aims, features, advantages, purposes, applications, embodiments, and the like will be apparent to those skilled in the art from the teachings of the present specification taken with the accompanying drawings.

The present invention is directed to improved technology for degassing foamed fermentation broths, particularly pressurized such broths, containing cultured microorganisms, without the use of defoaming agents and without appreciably damaging the cultured microorganisms.

Thus, in one aspect, the present invention provides a new and very useful method for degassing a fermentation broth which is foamed (that is, a liquid broth containing a dispersed gas phase which is mainly in the form of bubbles) and which contains cultured microorganisms. The method involves passing such broth while 
pressurized to least about 3 psig through a first spray nozzle means. This nozzle means discharges a spray suspension of such broth into a gaseous spray zone (or chamber) located in a gravitationally upper part of a degassing zone (or vessel). The spray zone is vented to the atmosphere.

This nozzle means is adapted to pass particulate bodies having an average particle size of at least about 0.0005 millimeters and to produce spray droplets having an average size of not greater than about 2.5 millimeters. In general, the nozzle means is chosen so that the individual discrete particles and/or droplets of the spray suspension issuing therefrom provides exposure in the gaseous spray zone of a maximal surface area relative to the volume thereof, thereby to enhance separation of gas from the liquid phase of the fermentation broth. The nozzle means, however, is also chosen so that, during the atomizing, no appreciable damage to, or hindrance to the passage therethrough of, microorganisms results. The nozzle size characteristics above indicated appear to accomplish these desired results.

The spray suspension from this nozzle means is coalesced in the degassing zone to form a bulk liquid phase located in a gravitationally lower portion thereof whereby the upper surface of such bulk liquid phase can be considered to form the bottom surface of such spray zone.

This liquid surface is characteristically covered by a layer of foam which itself has a surface. This nozzle means is so oriented that the spray suspension issuing therefrom is directed downwardly towards the surface of the bulk liquid phase and the surface of the foam layer thereon. The action of the downwardly moving spray suspension in striking the surface of the foam layer causes destruction of this foam surface and in effect results in further release and separation of gas from the liquid phase of the fermentation broth.

A substantial percentage (typically more than about 50% by volume) of the total releasable (separatable) gas present in a starting foamed fermentation broth is characteristically separated from the liquid phase of the fermentation broth by this sequence of spraying a directed spray suspension and coalescing.

Preferably, but optionally, a portion of such bulk liquid phase is continuously withdrawn from a gravitationally low region of such bulk liquid phase, mechanically pressurized (as with a pump), and passed through a second spray nozzle means located in the spray zone. This second spray nozzle means is similar in function and characteristics to the first spray nozzle means. The resulting second spray suspension is likewise downwardly directed towards the surface region of such foam layer. This recycling procedure enhances the degassification of such coalesced bulk liquid phase not only through the action of the second spraying and the coalescing thereof, but also through the action of the directed recycle spray suspension striking the surface of the foam layer and causing surface foam destruction.

The degassed fermentation broth is removed from a lower region of the liquid bulk phase collected in the degassing zone bottom region.

The degassing method of the invention can be practiced either batchwise or continuously (preferably the latter).

In another aspect, the present invention provides a new and very useful continuous process for accomplishing direct preparation of a degassed fermentation broth of cultured microorganisms which broth is adapted to be completely free from defoaming agents. In this process, water, nutrients, and air in respective selected amounts are charged continuously to a pressurized fermenting zone which has been inoculated with a selected microorganism species. The fermenting zone is maintained under controlled conditions of temperature, pressure, agitation, and dilution rate. Under continuous operating conditions, a heavily foamed fermentation broth is continuously removed from the pressurized fermenting zone at a generally constant rate and directly charged to a degassing zone of this invention through first spray nozzle means thereof in the manner indicated herein. Recycling of broth (through a second spray nozzle means) is preferably practiced in such degassing zone in the manner indicated herein. An effluent stream comprised of degassed product fermentation broth is withdrawn continuously and at a generally constant rate from the degassing zone which rate is generally equal to the rate at which the heavily foamed fermentation broth is withdrawn from such fermenting zone and charged to the degassing zone. The effluent stream so withdrawn from the degassing zone can be used as desired. For example, the broth can be pasteurized and then spray dried.

In another aspect, the present invention provides a new degassed fermentation broth having a high (in excess of 100 grams per liter) content of cultured microorganisms which is prepared directly and continuously in a two-zone preparation sequence.

In another aspect, the present invention is directed to new and very useful improved apparatus for accomplishing microorganism fermentation broth degassing.

In still another aspect, the present invention is directed to new and very useful apparatus for continuous pressurized fermentation and degassing using a combination of a pressurized fermentor and degassing apparatus of this invention.

Because of the surprising effectiveness of the present improved degassing technique and apparatus, process efficiency and economics for producing microorganisms are raised to levels not heretofore attainable.

BRIEF DESCRIPTION OF DRAWINGS

In the drawings forming a part hereof:

FIG. 1 is a diagrammatic representation partially in side elevation and partially in vertical section illustrating (a) one embodiment of degassifier apparatus of this invention, and (b) methods for using the same;

FIG. 2 is a simplified flow diagram illustrating one embodiment of a continuous fermentation and broth degassing process of this invention; and FIG. 3 is a simplified diagrammatic representation illustrating an apparatus configuration for practicing the process of FIG. 2;

DETAILED DESCRIPTION

Microorganisms

The processes of the present invention can be utilized with microorganisms capable of producing nontoxic proteins. Suitable microorganisms include bacteria, yeasts, and molds. Yeasts are presently preferred.

Suitable yeasts include species from the genera Candida, Kluyveromyces, Hansenula, Torulopsis, Saccharomyces, Pichia, Phaffia, Debaryomyces, Lipomyces, Crytococcus, Nematospora, and Brettanomyces. The preferred genera include Candida, Kluyveromyces, Hansenula, Torulopsis, Pichia Phaffia and Saccharomyces. Examples of suitable species of yeast include:

| | |
|---|---|
| *Candida boidinii* | *Hansenula saturns* |
| *Candida mycoderma* | *Hansenula californica* |
| *Candida utilis* | *Hansenula mrakii* |
| *Candida stellatoidea* | *Hansenula silvicola* |
| *Candida robusta* | *Hansenula polymorpha* |
| *Candida sake* | *Hansenula wickerhamii* |
| *Candida claussenii* | *Hansenula capsulata* |
| *Candida rugosa* | *Hansenula glucozyma* |
| *Brettanomyces petrophilium* | *Hansenula henricii* |
| *Hansenula minuta* | *Pichia membranefaciens* |
| *Hansenula nonfermentans* | *Pichia pinus* |
| *Hansenula philodendra* | *Pichia pastoris* |
| *Torulopsis candida* | *Pichia trehalophila* |
| *Torulopsis bolmii* | *Saccharomyces cerevisiae* |
| *Torulopsis versatilis* | *Kluyveromyces fragilis* |
| *Torulopsis glabrata* | *Saccharomyces rosei* |
| *Torulopsis molishiana* | *Bailii acidifaciens* |
| *Torulopsis nemodendra* | *Saccharomyces uvarum* |
| *Torulopsis nitratophila* | *Saccharomyces elegans* |
| *Pichia farinosa* | *Saccharomyces rouxii* |
| *Pichia polymorpha* | *Kluyveromyces lactis* |
| | *Phaffia rhodozyma* |

Suitable bacteria include species from the genera Bacillus, Mycobacterium, Lactobacillus, Leuconostoc, Streptococcus, Pseudomonas, Methanomonas, Brevibacterium, Acetobacter, Micrococcus, Corynebacterium, Achromobacter, and Methylobacter. Preferred genera include Bacillus, Pseudomonas, Protaminobacter, Lactobacillus, Leuconostoc, Streptococcus, Micrococcus, Arthrobacter and Corynebacterium.

Examples of suitable species of bacteria include:

| | |
|---|---|
| *Bacillus subtilus* | *Pseudomonas ligustri* |
| *Bacillus cereus* | *Pseudomonas orvilla* |
| *Bacillus aureus* | *Pseudomonas methanica* |
| *Bacillus acidi* | *Pseudomonas fluorescens* |
| *Bacillus urici* | *Pseudomonas oleovorans* |
| *Bacillus mycoides* | *Pseudomonas putida* |
| *Bacillus circulans* | *Pseudomonas boreopolis* |
| *Bacillus magaterium* | *Pseudomonas pyocyanea* |
| *Bacillus licheniformis* | *Pseudomonas methylphilus* |
| *Pseudomonas methanolica* | *Pseudomonas brevis* |
| *Pseudomonas acidovorans* | *Methylomonas agile* |
| *Pseudomonas methanoloxidans* | *Methylomonas albus* |
| *Protaminobacter ruber* | *Methylomonas rubrum* |
| *Methylomonas methanolica* | *Corynebacterium simplex* |
| *Mycobacterium rhodochrous* | *Leuconostoc bulgarions* |
| *Streptococcus cremoris* | *Lactobacillus bulgarions* |
| *Streptococcus lactis* | *Lactobacillus acidophilus* |
| *Streptococcus thermophilus* | *Corynebacterium alkanum* |
| *Leuconostoc citrovorum* | *Leuconostoc dextranicum* |
| *Corynebacterium hydrocarbooxydans* | *Mycobacterium phlei* |
| | *Corynebacterium oleophilus* |
| *Mycobacterium brevicale* | *Nocardia salmonicolor* |
| *Corynebacterium hydrocarboclastus* | *Nocardia minimus* |
| | *Nocardia corallina* |
| *Corynebacterium glutamicium* | *Nocardia butanica* |
| *Corynebacterium viscosus* | *Rhodopseudomonas capsulatus* |
| *Corynebacterium dioxydans* | *Microbacterium ammoniaphilum* |
| *Corynebacterium alkanum* | *Archromobacter coagulans* |
| *Micrococcus cerificans* | *Brevibacterium butanicum* |
| *Micrococcus rhodius* | *Brevibacterium roseum* |
| *Arthrobacter rufescens* | *Brevibacterium flavum* |
| *Arthrobacter parafficum* | *Brevibacterium lactofermentum* |
| *Arthrobacter simplex* | *Brevibacterium paraffinolyticum* |
| *Arthrobacter citreus* | *Brevibacterium ketoglutamicum* |
| *Methanomonas methanica* | *Brevibacterium insectiphilium* |
| *Methanomonas methanaooxidans* | |

Suitable mold include species from the genera Aspergillus, Monilia, Rhizopus, Penicillium, Mucor, Alternaria and Helminthosporium.

Examples of suitable species of molds include:

| | |
|---|---|
| *Aspergillus niger* | *Pencillium griseofulvum* |
| *Aspergillus glaucus* | *Penicillium expansum* |
| *Aspergillus flavus* | *Penicillium digitatum* |
| *Aspergillus oryzae* | *Penicillium italicum* |
| *Aspergillus terreus* | *Rhizopus nigricans* |
| *Aspergillus itconicus* | *Rhizopus oryzae* |
| *Pencillium notatum* | *Rhizopus delemar* |
| *Pencillium chrysogenum* | *Rhizopus arrhizus* |
| *Pencillium glaucum* | *Mucor mucedo* |
| *Rhizopus stolonifer* | *Mucor genevensis* |

Examples of suitable yeast species include *Candida utilis, Saccharomyces cerevisiae, Kluyveromyces fragilis, Saccharomyces uvarum, Phaffia rhodozyma* and *Pichia pastoris*. The most preferred microorganisms for use in the present invention include those yeasts which are currently approved by the FDA for human consumption.

Fermentation

Fermentation (or microbial culture) of chosen or selected microorganisms is accomplished in a fermentor apparatus (or fermenting zone) using a fermentation method.

The particular fermentation method and apparatus used to culture the chosen microorganism is not critical to the practice of the present invention. There are numerous fermentation processes and apparatuses that are well known to those skilled in the art, both batch and continuous. Any of these well known fermentation processes and fermentors are suitable for use with the present invention, provided such is/are appropriate for the particular microorganism being cultured (as those skilled in the art will readily appreciate). It is preferred to use a freshly prepared foamed fermentation broth in the practice of this invention.

Examples of suitable fermentors and fermenting processes are described, for example, in Perry's Chemical Engineer's Handbook Sixth Edition (copyright 1984) published by McGraw Hill, Inc., New York, N.Y. at pages 27-5-27-13.

Typically microorganisms are cultured under aqueous phase conditions by growing them on a suitable nutrient composition which typically includes a carbon and energy source, an assimilable nitrogen source, mineral salts, molecular oxygen (usually derived from air) with suitable pH maintenance, and with other growth factors optionally being present, if desired, as those skilled in the art will readily appreciate.

Typically, the nutrient composition may vary depending upon such factors as the microorganism species being cultured, nutrients available, and the like. Selection of nutrients for a given such composition for use in culturing a particular microorganism species is known to those skilled in the art (see for example the "Manual of Methods for General Bacteriology," American Society for Microbiology, Washington, D.C., and "Yeast: Characteristics and Identification," Cambridge University Press, Cambridge, GB).

The degassing technique and apparatus of the present invention are particularly well suited for use with pressurized fermentations involving high (at least about 2 VVM) air flow, operated either continuously (preferred) or batchwise.

Suitable and presently preferred batch and continuous fermentation conditions are illustrated in Table I below:

TABLE I

Fermentation Conditions

| Condition (or Variable) | Range Broad | Range Preferred |
|---|---|---|
| Temperature (°C.) | 20-60[6] | 25-50[6] |
| Pressure psig[3] | 0-70 | 5-50 |
| Retention Time (hour)[1] | 1-40 | 2-15 |
| pH | 2-7 | 3-7 |
| Agitation (rpm)[5] | 100-1200 | 400-800 |
| Aeration (vvm)[2] | 2-7 | 3-5 |
| Dilution Rate ($h^{-1}$)[1][4] | 0.025-1 | 0.067-0.5 |
| Total nutrients (dry weight, grams per liter) | 50-700 | 100-400 |

Table I footnotes:
[1] Applies when continuous fermentation is carried out.
[2] "vvm" indicates ratio of volume of air input (measured at atmospheric pressure) to volume of fermentor broth.
[3] "psig" indicates pounds per square inch gauge.
[4] "$h^{-1}$" indicates reciprocal hours.
[5] Using a turbine bladed agitator or equivalent.
[6] Where the upper temperature in any given fermentor is chosen so as to be substantially non-lethal to the particular microorganisms being cultured.

One presently preferred fermentation procedure for use in the practice of the present invention is shown and described in Wegner U.S. Pat. No. 4,617,274 entitled: "Biochemical Conversions by Yeast Fermentation at High Cell Densities", which teaches a pressurized fermentation technique, and which is incorporated by reference.

It is presently very much preferred to practice pressurized fermentation when using the degassing technique and apparatus of this invention. For one thing, the need for a pump to pressurize a foamed fermentation broth is not then needed since the pressure existing in the fermentor itself is sufficient to transport effluent from the fermentor to the degasser and the first atomizing nozzle thereof. This direct interconnection avoids the problems of trying to pump or pressurize a foamed fermentation broth before feeding such to the first atomizing nozzle.

Fermentation Broth

The product of a microbial fermentation procedure is conventionally termed a fermentation broth. Such a broth is characterized by being composed of:
- spent culture medium (usually expressed on a dry solids basis)
- dispersed gas (in the medium mainly as bubbles or foam)
- cultured microbial cells (suspended in the medium)
- fermentation by-products (mainly dissolved in the medium)
- water Broadly, a fermentation broth contains from about 5 to 180 grams per liter of harvestable cultured microorganisms (or microbial cells). When the operating conditions of Table I are practiced, the product fermentation broth is comprised as shown in Table II. Such a broth comprises a starting system or material adapted for use in the practice of the degassing technique of the present invention.

TABLE II

Foamed Fermentation Broth Characterization

| Component (or variable) | Range Broad | Range Preferred |
|---|---|---|
| Spent medium solids[3] (dry weight, in g/L,[2] of degassed broth) | 0-25 | 5-15 |
| Cultured Microbial cells (dry weight, g/L, degassed broth) | 5-180 | 100-160 |
| Fermentation by-product solids (dry weight, g/L, degassed broth) | 0-100 | 0-15 |
| Dispersed gas bubbles (measured at atmospheric pressure) (%, v/v)[1] | 20-60 | 40-55 |
| Water (g/L, degassed broth) | 100-900 | 300-850 |

Table II footnotes
[1] % v/v indicates volume of gas per unit volume of liquid multiplied by 100 (e.g. volume percent of gas per liter of broth).
[2] g/L indicates grams per liter.
[3] "Spent medium" includes any unconsumed nutrients.

As can be seen from Table II, the preferred starting fermentation broths are characterized by having a relatively high microbial cell content which is preferably in excess of 100 grams per liter as well as by having a relatively high dispersed gas content.

In this invention, the problem of separating gas from a starting fermentation broth having a high dispersed gas (foam) content is solved by the use of the new and very useful degassing procedure and the associated new apparatus provided herein.

Degassification

Degassification of a fermentation broth, such as above characterized, is carried out in accord with the teachings of the invention.

Figure 1:
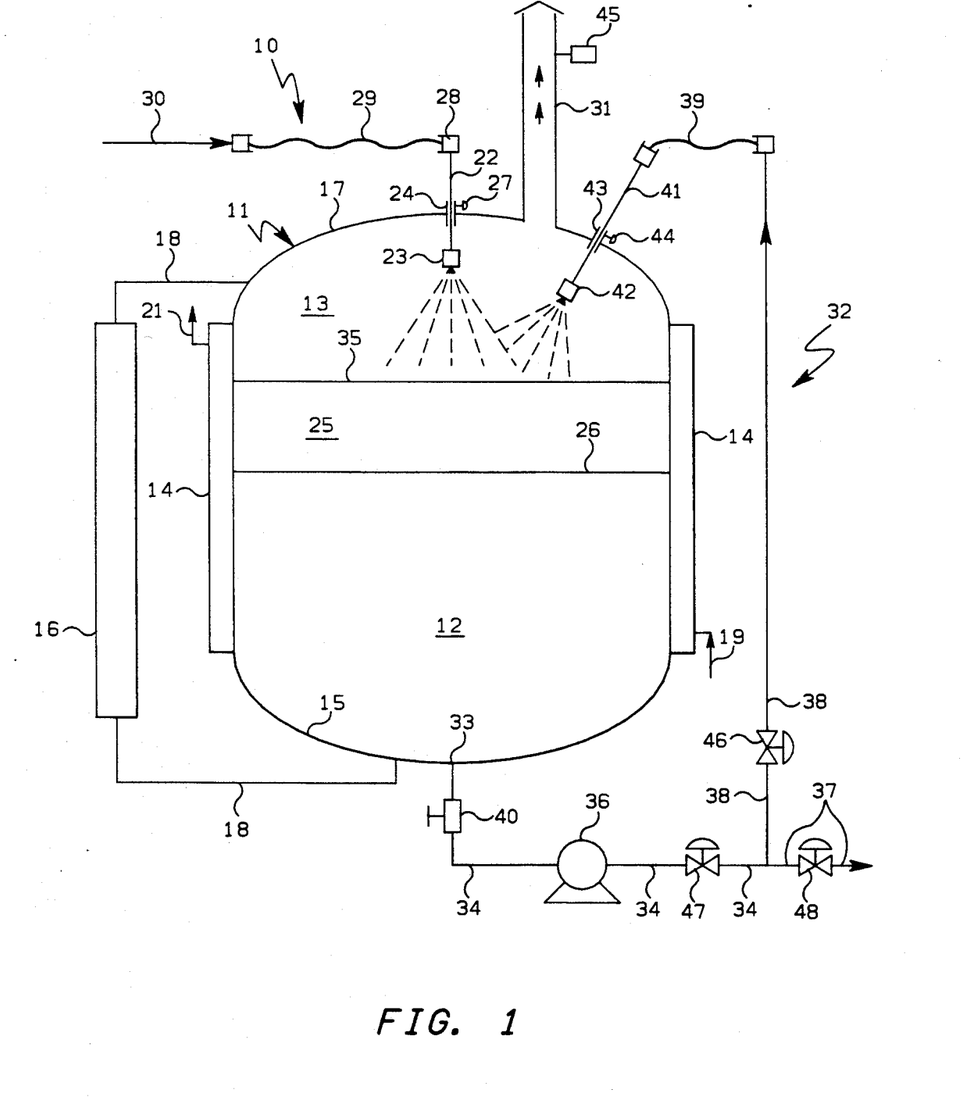

Referring to FIG. 1, there is seen one embodiment of degasser apparatus of this invention which is herein designated in its entirety by the numeral 10. Degasser apparatus 10 incorporates a tank 11 which is preferably fabricated of stainless steel, or of glass lined steel, or of other materials which provide interior wall surfaces which are substantially inert to such materials as microorganisms, the broth holding the same, and the like. Preferably, the bottom wall surfaces 15 of tank 11 are sloped (as shown) to a drain aperture or port 33 for ease in draining fluid from tank 11, such as degassed, sprayed, coalesced and collected liquid broth 12, and also the top wall surfaces 17 of tank 11 are preferably dome configured (as shown), or conically tapered (not shown), for similar reasons and also for purposes of providing an overhead gas or vapor space 13. Preferably the tank 11 has a generally cylindrical mid-portion and is generally cross-sectionally circular relative to a longitudinal axis and wherein said vessel has a ratio of average diameter in said mid-portion to said longitudinal axis ranging from about 1:1 to 5:1.

Tank 11 is provided with a jacket 14 circumferentially extending around side wall portions thereof through which a temperature regulating coolant liquid, such as water, glycol, mixtures thereof, or the like, can be circulated via input line 19 and output line 21 to control the temperature of liquid broth 12 in tank 11. Usually jacket 14 is used to remove heat from broth 12. Also, tank 11 is preferably provided with a sight glass 16 which is conveniently interconnected with a location in bottom wall surfaces 15 and with a location in top wall surfaces 17 by pipes 18, thereby permitting an operator to observe the liquid level in tank 11 during operation of degasser apparatus 10. If desired, an observation window (not shown) can be placed at a location in top wall surface 17.

Through a central upper location in top wall surfaces 17 an input pipe 22 extends which terminates in space 13 in an associated atomizing nozzle 23. Preferably, the pipe 22 slidably extends through a sleeve 24 that is fixed by welding or the like to adjacent top wall surfaces 17 and pipe 22 is thus slidably extendable or retractable through sleeve 24 so as to permit the spatial location of nozzle 23 relative to the upper surface 26 of liquid 12 to be adjustable. A set screw 27 or the like threadably mounted through sleeve 24, or some other equivalent arrangement, is used to clamp pipe 22 in a desired set position. The outer end 28 of pipe 22 is functionally associated with a flexible tube 29 by coupling means (not shown), and tube 29 similarly joins an input feed pipe 30. More than one input nozzle can be provided if desired. In operation of degasser apparatus 10, a pressurized gas-bubble containing (or foaming) fermentation broth is charged into tank 11 through the sequence of tube 29, pipe 22, and nozzle 23. The atomized fermentation broth in space or chamber 13 condenses and/or coalesces in tank 11 to form collected liquid broth 12 in a lower portion of tank 11. The atomization resulting from passage of the fermentation broth through nozzle 23 functions as a foam-breaking technique. The vapor space 13 is maintained at ambient (atmospheric) pressure by vent means associated with from vapor space 13, the vent means here being illustratively provided by vent pipe or duct 31 associated with an upper central location of top wall surfaces 17. If desired, and as shown, an exhaust fan 45 is associated, for example, with an upper end portion of duct 31 to assure the maintenance of a positive air flow therethrough and an ambient pressure in space 13 during operation of apparatus 10.

In practice, it is found convenient and preferable to maintain the position of liquid surface 26 relative to the side walls of tank 11 such that surface 26 falls in the range from about 1/5 to 4/5 of the distance from the top most interior location of tank 11 (relative to the total interior height of tank 11); however, any convenient liquid level can be used. Characteristically, surface 26 is covered by a layer 25 comprised of foam. Not only does the tank 11 thus serve as a holding tank adapted to accommodate an emergency or temporary interruption in a degassing process of this invention, such as hereinbelow described, but also the tank 11 serves to maintain a quantity of collected liquid broth 12 in tank 11 from whose surface 26 residual quantities of gas can escape by effervescence, which is desirable.

The nozzle 23 is oriented (or directed) towards the surface 26. The spray suspension issuing from the oriented nozzle 23 is directed against the upper surface 35 of the foam layer 25 which serves to cause a break up of surface foam cells in foam layer 25, which is desirable.

In operational practice, it is preferred to provide degasser apparatus 10 with an optional recycle loop which is designated in its entirety by the numeral 32. While many different apparatus configurations for recycle loop 32 are possible, as those skilled in the art will readily appreciate, the apparatus 10 embodiment is provided with a recycle loop 32 which comprises in connected succession line 34, pipe 38, flexible tube 39, pipe 41, and second atomizing nozzle 42. The subassembly of tube 39, pipe 41, and nozzle 42 is similar to the above described subassembly of tube 29, pipe 22, and nozzle 23 in structure and operation; thus, pipe 41 slidably adjustably moves and extends through sleeve 43 with set screw 44 mounted in sleeve 43 being used to position and clamp pipe 41. More than one recycle loop or recycle nozzle means can be used if desired. In apparatus 10, the piping arrangement used is thus such that only a single pump 36 is used to remove liquid broth from tank 11 both for discharge of effluent (as for further processing) and for recycle. If desired, alternatively, one pump can be used for effluent control and a second pump can be used for recycle control, for example. An adjustable valve 46 in line 38 is conveniently provided to aid in regulating the recycle rate. Also, flow regulating valves 47 and 48 can optionally be provided in line 34 between pump 36 and pipe 38, and in discharge line 37 after line 38, respectively.

Thus, if recycling is practiced, the recycle rate can be independently regulated separately from the discharge rate, if desired. The recycle loop 32 is found to enhance the separation of gas from fermentation broth particularly when pressurized fermentation broths are continuously charged to the degassing zone. Use of the recycle loop 32 is preferred when it is desired to separate as much as practical of the gas present in a fermentation broth entering tank 11 through line 30, tube 29, pipe 22, and nozzle 23 The recycle loop 32 is particularly preferred when foam-filled fermentation broth from a pressurized fermentor is being continuously charged to degasser apparatus 10.

Collected liquid broth 12 which has been degassed in apparatus 10 is removed from tank 11 through the port 33. Port 33 feeds into take-off line 34. Conveniently, line 34 is equipped with a pump 36 which has the capacity to produce adjustable flow rates and adjustable output pressures (such as a variable speed centrifugal pump), thereby permitting the rate and the pressure at which liquid broth 12 is withdrawn from tank 11 to be regulated and controlled in a desired manner. Between port 33 and pump 36, an adjustable throttle valve 40 or the like is located for purposes of regulating effluent removal from tank 11 through port 33. Instead of being recycled, effluent from pump 36 can pass into line 34 and then into discharge line 37 which leads to downstream processing zones or stations. For example, effluent from discharge line 37 can be pasteurized to kill the microorganisms cultured, and then the resulting effluent can be spray dried to recover dried cultured microorganism residues, as those skilled in the art will appreciate.

As those skilled in the art will appreciate, the degasser apparatus and degassing process of this invention can be employed for degassing fermentation broths of widely different composition under widely variable entering pressures, whether continuous or batch operating conditions are contemplated. A non-pressurized fermentation broth can be pressurized by a feed pump and then passed through nozzle 23. For low charging pressures (such as under about 10 lbs/in$^2$ gauge (psig)) and low gas volumes (under about 20% V/V), a single stage of atomization using the tank 11 may be sufficient without utilization of a recycle loop to effectuate a desired level of gas removal from entering or starting fermentation broth. Use of a combination of two stages of atomization in a single degassing tank (one stage being atomization of the input stream and another stage being the atomization of the recycle stream) as taught herein has been found capable of achieving substantially complete degassing of a pressurized fermentation broth, depending upon conditions and circumstances. For example, a starting broth under a pressure of 40 psig or higher, and having a total solids content (dissolved and suspended) of greater than about 7.5 weight percent, and having a gas content of greater than about 50 volume percent (all based on total fermentation broth) can be degassed; however, substantially higher or lower operating degasser input pressures, solids contents, and gas contents appear to be feasible with suitable degasser apparatus embodiments of this invention.

While the vapor space 13 is preferably maintained at atmospheric pressures during operation of apparatus 10, as indicated, those skilled in the art will appreciate that the vapor space 13 can be maintained at subatmospheric pressure or super atmospheric pressure if desired during such operation. However, subatmospheric pressures now appear to have tendency to cause operating problems apparently caused by excessive foam production, while super atmospheric pressures appear to result in higher operational costs since depressurizing to atmospheric pressures is only postponed to a subsequent stage, such as a second degassing stage. A second degassing stage connected in series with a first degassing stage appears to have no functional or processing advantage at this time. Thus, apparatus 10 is useful for degassifying fermentation broths either produced at ambient or low pressures or produced at elevated pressures. Continuous operating conditions are preferred.

Illustrative degassing apparatus operating conditions adapted for degassing in accord with process of the present invention (preferably using a continuous input feed of foamed fermentation broth) are shown in Table III below:

TABLE III

Degassification Process Parameters

| Condition (or Variable) | Ranges Broad | Preferred |
| --- | --- | --- |
| Nozzle size (mm) | 0.0005–2.5[1] | 0.001–3[1] |
| First Nozzle pressure (psig) | 3–100 | 5–50 |
| Starting temperature °C.[2] | 20–60 | 25–50 |
| Interior temperature °C.[3][4] | 0–60 | 4–50 |
| Second Nozzle pressure (psig) | 1–50 | 5–45 |

Table III footnotes:
[1] The lower value indicates the average minimal particle size presented in suspended form in a starting fermentation broth which can be passed through a nozzle orifice, while the upper value indicates the average maximum droplet size which is produced after passage of a starting fermentation broth through an atomizing nozzle.
[2] The starting temperature referenced is the temperature of a fermentation broth entering the first spray nozzle in the degasser apparatus (from the fermentor).
[3] The interior temperature referenced is the interior temperature of the degassing zone (both the liquid phase and gas chamber).
[4] A zero temperature here means "above freezing" as regards the broth.

Characteristically, by the practice of the present invention, one can obtain at least about a 90% reduction in gas volume in a fermentation broth compared to a starting foamed fermentation broth (such as one from a pressurized fermentor operated with high air circulation) containing at least about 40% by volume of gas.

Illustrative conditions for practicing the presently most preferred continuous high pressure fermentation and degassing process of this invention are provided in Table IV below. The fermentation broth produced by the Table IV continuous fermentation conditions has characteristics as set forth in the "preferred" ranges shown in Table II above.

TABLE IV

Operating Process Conditions for High Pressure Continuous Fermentation and Degassing

| Process Variable | Range |
| --- | --- |
| (Fermentation) | |
| pressure (psig) | 20–50 |
| temperature (°C.) | 20–40 |
| agitation (rpm) | 500–800 |
| ammonia input (g/g cells) | 0.8–1.2 |
| air input (vvm) (40 psig base) | 3–6 |
| dilution rate (h$^{-1}$) | 0.17–0.25 |
| retention time (hr) | 4–6 |
| water | to chosen level |
| total nutrient materials (grams per liter of gas-free water) | 100–400 |
| (Degassification) | |
| charging pressure (psig) | 5–40 |
| chamber gas pressure (psig) | 0.8–1.2 |
| recycle flow rate (gpm) | 0.5–30 |
| recycle charging pres. (psig) | 5–10 |
| chamber temperature (°C.) | 4–10 |
| discharge rate (gpm) | 0.5–30 |

As those skilled in the art will appreciate, the broth retention time in the degassifier is variable over a very wide range depending upon many factors, especially the growth rate of the particular microorganisms being cultured. The fermentor temperature conditions shown in Table V, as those skilled in the art will appreciate, are particularly suitable, for instance, for yeasts. Bacteria, for example, can be cultured at higher temperatures, such as 70° C. or even higher. Also, the cooling temperature of 0 referenced in Table V here means "above freezing".

The degassed fermentation broth produced by the process summarized in Table IV characteristically has more than about 90% of the gas present in the starting heavily foamed fermentation broth separated therefrom and contains more than about 100 grams per liter of cultured microorganisms.

Figure 2:
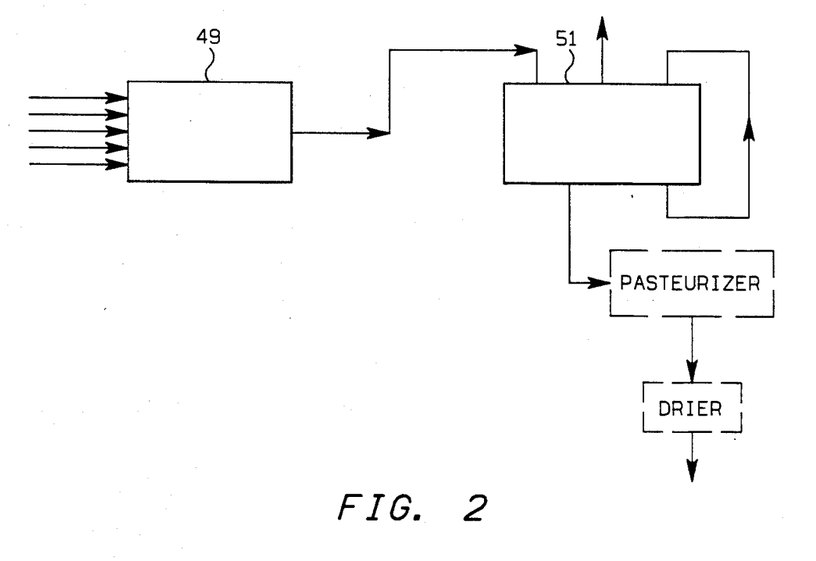
Figure 3:
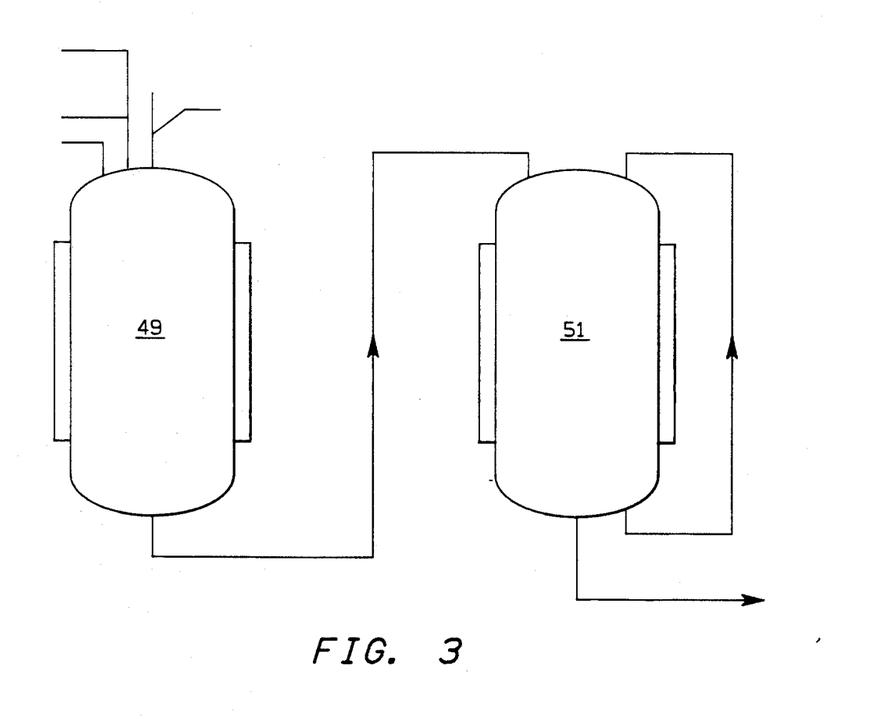

Referring to FIGS. 2 and 3, there is seen one embodiment of a preferred integrated continuous process for effecting fermentation of microorganisms under high pressure with high air flow followed by degassing of the resulting heavily foamed fermentation broth. Apparatus for practicing this process is shown in FIG. 3. The process and apparatus employs a single fermentation zone and a single immediately succeeding interconnected degassing zone. In the degassing zone, the degassing techniques and apparatus of this invention are utilized. In the fermentation zone, the fermenting techniques and apparatus known to the prior art are utilized. For example, one suitable fermentation apparatus is described in Wegner and Hunt U.S. Pat. No. 4,670,397; the disclosure of which is hereby incorporated by reference.

Prior to the present invention, so far as now known, no alternative combination of technique and apparatus were known which were suitable for achieving the objectives of (a) accomplishing the desired and preferred highly efficient continuous high pressure fermentation with high air flow and resultant production of a high solids content fermentation broth, (b) subsequently accomplishing a preferably desired continuous substantially complete degassing of a foam-filled fermentation broth without using any chemical defoaming agents (c) using only a single continuously operating fermenting zone directly coupled to a single continuously operating degassing zone, and (d) fermenting and degassing without causing any damage to the cultured microorganisms.

In practicing the continuous process shown in FIG. 2, using the apparatus shown in FIG. 3, as those skilled in the art will appreciate, the particular microorganism being cultured is preliminarily inoculated into the fermentor (an inoculum having been suitably preliminarily cultured in auxiliary apparatus). In a start up procedure, the fermentor is gradually brought up to the continuous operating conditions such as shown in Table IV. Thereafter, the effluent from the fermentor is continuously and directly charged into the degassifier which is operated under the conditions shown in Table IV.

In FIGS. 2 and 3, the fermentor 49, duly inoculated with a chosen microorganism for culturing, is continuously charged with oxygen, nutrients and water, for example, a diluted aqueous sucrose stream, an aqueous nutrient/salt stream, an aqueous trace mineral stream, and a gas stream comprised of a compressed air suitably controlled by dissolved oxygen in the fermentor, a gas stream comprised of a compressed ammonia controlled by internal fermentor pH (both gas stream being charged by sparging). The conditions of fermentation are selected so as to maintain in the fermentation zone no excess sucrose yet maintain the amount of sucrose supplied equal to the maximum effective amount which the microorganisms can consume (metabolize). If an excess of sucrose were to be allowed, then alcohol would be produced as a by-product which is undesirable. On the other hand, if less than the maximum usable amount of sucrose is supplied relative to the microorganisms being cultured, then maximum microorganism productivity is not achieved.

The effluent from the fermentor unit 49 is conveyed (moved) by a conduit directly and continuously to the degassification unit 51 and therein atomized (sprayed) as taught herein. After the coalesced liquid level in the degassifier reaches a desired operating height, as at the end of a start up procedure, then a recycle procedure is started and maintained in the degasser unit. Conditions are shown in Table IV.

EXAMPLES

The following examples are presented in further illustration of the invention and are not to be considered as unduly limiting the scope of the invention.

EXAMPLE 1

Continuous Fermentation

In a continuous aerobic fermentation process, dilute aqueous sucrose, dilute aqueous mineral salts, compressed air, and compressed anhydrous ammonia were charged to a 1500 liter capacity fermentor that had been inoculated with the yeast Candida utilis NRRL Y-1082. The fermentor was operated under a pressure of about 40 psig, and a constant weight was maintained in the fermentor by automatic fermentor weight control so that the volume of the foam-filled fermentation broth in the fermentor was about 720 liters.

The pH was maintained automatically at about 4.0 by the ammonia addition. The temperature in the fermentor was maintained at about 35° C. by cooling coils in the fermentor and in a jacket around the outside walls of the fermentor. The pressure was maintained automatically by compressed air sparging into the fermentor. The air aeration rate was about four volumes of air (charged at about 60 psig and about 25° C.) per volume of fermentor broth per minute. Agitation sufficient to maintain the fermentor broth in the reactor in a substantially uniform state was accomplished by two paddle-type turbine blades mounted on a common shaft in axially spaced relationship to one another, the shaft being generally vertically disposed in the fermentor along the fermentor vertical axis, and the shaft being driven at about 800 rpm by an external powerhead.

Under steady-state conditions foam-filled fermentor broth was continuously withdrawn from a bottom part in the fermentor through a controllable harvest valve. It was found that the high gas content of the so-withdrawn effluent made such difficult to transport by pipe using a pump.

The gas content (foam derived) of the effluent fermentor broth was not exactly known, but from the following tests, it was estimated that the gas volume of the effluent broth was generally in the range of 40-60% v/v measured at atmospheric pressure:

Test a: An aliquot of the fermentation broth was removed from a sampling valve located in the fermentor wall amount about ⅓ of the way up from the bottom thereof and its volume was immediately measured and found to be 1060 mL. To this sample, silicone-based antifoam (4 drops) was added followed by gentle agitation to ensure a uniform mixing of said antifoam. After standing at about 25° C. for 4 minutes, the total liquid volume of the resulting sample was found to be 600 mL. The foam (gas) volume was then calculated as 460 mL or 43.4% of the fermentation broth.

Test b: An aliquot of the fermentation broth in the effluent stream was collected from the region of the harvest valve. The total broth volume was immediately measured and found to be 1400 mL. To this fermentation broth, 4 drops of an antifoam was added as in test (a) followed by gentle agitation. After standing at about 25° C. for four minutes, the total liquid volume was found to be 680 mL. The foam (gas) volume was then calculated as 720 mL or 51.4% of the fermentation broth discharged from the harvest valve.

The effluent stream from the harvest valve of the pressurized fermentor was continuously fed directly through a conduit to a degasser apparatus of the type shown in FIG. 1 and charged through the first spray nozzle. The nozzle was able to pass particulates having an average particle size down to about 0.0005 mm and was able to develop spray droplets not larger than about 2.5 mm. The nozzle used was purchased commercially from the Spraying Systems Company under the trade designation "Fulljet" ⅛ GG-25. The spray suspension from the nozzle was directed downwardly towards the surface of the foam layer which characteristically appeared on the surface of the coalesced liquid collected in the lower regions of the degasser apparatus. Under continuous operating conditions, with no recycling, the nozzle head was spaced at a distance of about 50 centimeters from the surface of the foam layer, and a degassed effluent stream was continuously removed from the degasser apparatus at a rate sufficient to maintain a constant level of coalesced liquid in the degasser apparatus (which was also about equal to the rate at which the liquid phase of the fermentor broth was being withdrawn through the harvest valve). The temperature of the coalesced liquid in the degasser apparatus is maintained at about 5° C. by circulation of glycol/water coolant in the jacket 14 of apparatus 10 (FIG. 1).

Under substantially steady-state continuous operating conditions, an aliquot sample (1000 milliliters immediately measured) of such effluent stream from the degasser was collected. To this sample, four drops of the antifoam agent used in Tests (a) and (b) above were added followed by gentle agitation. After standing at 
about 25° C. for four minutes, the total liquid volume of the resulting sample was found to be 800 mL. The calculated form or gas volume of the thus collected broth was 200 mL or 20% of total broth volume. This represents a gas separation of more than 60% by gas volume, compared to the results shown by test(b) above.

When the effluent from the degassifier apparatus was examined under a microscope, it was found that the cultured microorganisms have experienced no noticeable deterioration or physical damage as a result of the foregoing degassing procedure (compared to a corresponding examination of the cultured microorganism, present in the effluent from the fermentor).

EXAMPLE II

The procedure of Example I is continued except that recycle of coalesced liquid in the degasser apparatus was undertaken using the recycle loop (32) as in apparatus 10 of FIG. 1. The rate of continuous recycle was chosen to be about equal to the rate at which effluent was continuously withdrawn from the degasser apparatus. The second atomizing nozzle was the same as the first atomizing nozzle (above described in Example I) and such second nozzle was likewise spatially oriented so that the spray suspension produced therefrom is directed toward the surface of the foam layer. The distance between the nozzle and the foam layer was set at about 50 cm. The pressure before the second nozzle was about 5 psig (achieved by operation of pump 36).

Under steady state continuous operating conditions, with such recycle, an aliquot (1000 mL immediately measured) was separated from the continuous effluent stream being removed from the bottom of the degasser apparatus. Using the same procedure as described above in Example I for foam measurement, it was found that the calculated foam (gas) volume was 100 mL or 10% of the broth volume. This represents a reduction of over about 80% in gas volume when compared to the result obtained in Example I(b) above. When the effluent from the degassifier apparatus was examined, under a microscope, it was found that the cultured microorganisms have experienced no noticeable deterioration or physical damage as a result of the foregoing degassing procedure (compared to a corresponding examination of the cultured microorganism, present in the effluent from the fermentor).

EXAMPLE III

The following fermentation procedure is believed to be typical and illustrative of continuous fermentation of microbes:

To a fermentor are charged:

5 to 35 parts by weight sucrose 1 to 20 parts by weight mineral salts 45 to 94 parts by weight water.

An inoculum of *C. utilis* yeast is added to this mixture.

The fermentor is sealed, agitation is started (twin paddle-type turbines on a single shaft rotating at about 600 rpm), and air is sparged into the system at 25° C. at a rate of about 45 psig so that the aeration rate is about 3 volumes per volume of liquid ferment per min. Also ammonia is introduced at a rate sufficient to maintain pH at about 4° Fermentor temperature is maintained at about 35° C. through heat exchange coolant circulation.

The product broth is charged into a degasser apparatus similar to that used in Example I with recycle and it is found that most of the gas in the broth is separated from the broth liquid and no adverse effects upon the microorganisms is observed.

EXAMPLE IV

Batch Fermentation and Degassing

Yeast grown in a batch mode in a 1,500 liter fermentor is used for this calculated illustrative embodiment. Initially, the duly-sterilized 1,500 liter fermentor is loaded with 400 Kg of feed, and then is inoculated with 12 l of inoculum containing about $1.2\times10^{14}$ of the same *C. utilis* yeast species indicated in Example I. The inoculum is grown in a small bench top fermentor. The inoculated 1500 liter fermentor is operated aerobically at about pH 4.0 and about 35° C. until all of the carbon source (sucrose) is consumed. Sterile additional nutrient feed is then continuously added at a rate such that the culture is able to completely consume the carbon source as added, as monitored by dissolved oxygen response. The air added is sterilized by filtration and sparged into the liquid fermentor at a rate of about 2 volumes per volume of gaseous ammonia is used to control the pH and provides the nitrogen source. When the fermentor weight reaches 800 Kg, the feed is discontinued and the whole fermentor content is discharged through the harvest value for degassing directly into a degasser apparatus similar to that used in Example I.

Recycle is employed. The coalesced liquid removed from the degasser bottom contains very few gas bubbles and the cultured microorganisms appear to show no effects caused by the degassing procedure.

While this invention has been described in detail for the purpose of illustration, it is not to be construed as limited thereby, but is intended to cover all changes and modifications within the spirit and scope thereof.

That which is claimed is:

1. A process for degassing a starting fermentation broth containing a dispersed gas phase in the form of bubbles and suspended cultured microorganisms comprising the steps of:

(a) providing a degassing apparatus comprising: a generally fluid-tight vessel defining a degassing zone, said degassing zone having a gravitationally upper portion and a gravitationally bottom portion; first spray nozzle means in flow communication with said upper portion and constructed so as to pass particulate bodies having an average particle size of at least about 0.0005 millimeters and to produce spray droplets having average sizes not greater than about 2.5 millimeters; vent means in flow communication with said upper portion; and recycle means providing flow communication between said bottom portion and said upper portion and including second spray nozzle means in flow communication with said upper portion and constructed so as to pass particulate bodies having an average particle size of at least about 0.0005 millimeters and to produce spray droplets having average sizes not greater than about 2.5 millimeters;

(b) charging a starting fermentation broth containing a dispersed gas phase in the form of bubbles and suspended microorganisms under a pressure of at least about 3 psig through said first spray nozzle means so as to form a first spray suspension, said first spray suspension having a bottom surface;

(c) coalescing said first spray suspension to form a bulk liquid phase in said bottom portion of said degassing zone, said bulk liquid phase having a gravitationally upper portion, a gravitationally bottom portion and an upper surface whereby said upper surface of said bulk liquid phase forms the bottom surface of said first spray suspension;

(d) directing said first spray suspension downewardly towards said upper surface;

(e) removing a first portion of said bulk liquid phase from said bottom portion of said degassing zone;

(f) pressurizing said first portion of said bulk liquid phase to from about 1 to 50 psig;

(g) discharging said first portion of said bulk liquid phase through said second spray nozzle means so as to form a second spray suspension; and (h) coalescing said second spray suspension into said bulk liquid phase, said second spray suspension being directed towards said upper surface.

2. A process of claim 1 wherein said charging pressure ranges from about 5 to 50 psig while maintaining said starting fermentation broth at a temperature ranging from about 20° to 50° C. and said starting fermentation broth is derived from a pressurized fermentation.

3. A process of claim 2 wherein a second portion of said bulk liquid phase is continuously removed and separated from said gravitationally bottom portion thereof.

4. A process of claim 3 wherein, after said upper surface initially reaches a level within a predetermined range in said vessel, said charging and said second portion removing are each carried out at approximately constant and equal rates.

5. A process of claim 4 wherein said first portion is removed, pressurized, and discharged through said second nozzle means at a rate such that said second portion which is removed and separated is at least about 90% by volume free from the dispersed gas phase associated with said starting fermentation broth measured at atmospheric pressure.

6. The process of claim 5 wherein said first portion and said second portion are simultaneously withdrawn as a single common stream from a common location in said bottom portion of said degassing zone which common stream is then divided into said first portion and said second portion.

7. The process of claim 1 wherein interior portions of said vessel are maintained at a temperature ranging from above 0° to about 60° C.

8. The process of claim 1 wherein said starting fermentation broth is comprised of;
(a) from 0 to about 25 grams per liter of degassed fermentation broth on a dry weight basis of spent medium solids,
(b) from about 5 to 180 grams per liter of degassed fermentation broth on a dry weight basis of cultured microbial cells,
(c) from 0 to about 100 grams per liter of degassed fermentation broth on a dry weight basis of fermentation by-products,
(d) from about 20 to 60 volume % of gas per liter of said foamed fermentation broth, and
(e) from about 100 to 900 grams per liter of degassed fermentation broth of water.

9. The process of claim 1 wherein said starting fermentation broth is prepared in a fermentation zone at a temperature of from about 20° to 60° C., provided the upper temperature in any given fermentation so as to be substantially non-lethal to the particular microorganisms being cultured, at a pressure of from 0 to about 70 psig, at a pH of from about 2 to 7, while charging to said fermentation zone from about 2 to 7 volumes of air per fermentation zone volume per minute and while maintaining in said fermentation zone a turbine-bladed agitator operating at from about 100 to 1200 rpm.

10. A continuous process for the direct preparation of a degassed fermentation broth which contains in excess of about 100 grams per liter of cultured microorganisms and which is substantially free from defoaming agents, said process comprising the steps of continuously and sequentially:

(a) providing a fermentation apparatus defining a fermenting zone, said fermenting zone including a growing microorganism species;

(b) charging into said fermenting zone:
(1) water in an amount sufficient to maintain a predetermined liquid level in said fermenting zone,
(2) from about 100 to 400 grams of total nutrient materials on a dry weight basis per liter of gas-free water,
(3) from about 3 to 6 volumes of air per volume of said fermenting zone per minute based upon 40 psig;

(c) maintaining in said fermenting zone a dilution rate of from about 0.17 to 0.25 per hour, a pressure of from about 20 to 50 psig, a temperature of from about 20 to 40 degrees C., and at least sufficient agitation to keep the materials in said fermenting zone in a substantially uniformly mixed condition;

(d) removing at said temperature and said pressure from said fermenting zone the resulting foamed fermentation broth, said broth being comprised of the following:
(1) from about 300 to 850 grams of water per liter of degassed broth,
(2) from about 100 to 160 grams of dry weight microorganisms per liter of degassed broth,
(3) from about 5 to 15 grams of spent broth solids per liter of degassed broth,
(4) from 0 to about 15 grams of dry weight fermentation by-products per liter of degassed broth, and
(5) from about 40 to 55 volume percent of dispersed, discrete gas bubbles;

(e) providing a degassing apparatus comprising: a generally fluid-tight vessel defining a degassing zone, said degassing zone having a gravitationally upper portion and a gravitationally bottom portion; first spray nozzle means in flow communication with said upper portion and constructed so as to pass particulate bodies having an average particle size of at least about 0.0005 millimeters and to produce spray droplets having average sizes not greater than about 2.5 millimeters; vent means in flow communication with said upper portion; and recycle means providing flow communication between said bottom portion and said upper portion and including second spray nozzle means in flow communication with said upper portion and constructed so as to pass particulate bodies having an average particle size of at least about 0.0005 millimeters and to produce spray droplets having average sizes not greater than about 2.5 millimeters;

(f) charging said foamed fermentation broth through said first spray nozzle means so as to form a first spray suspension, said first spray suspension having a bottom surface;

(g) coalescing said first spray suspension to form a bulk liquid phase in said bottom portion of said degassed zone, said bulk liquid phase having a gravitationally upper portion, a gravitationally bottom portion and an upper surface whereby said upper surface of said bulk liquid phase forms the bottom surface of said first spray suspension;

(h) directing said first spray suspension downwardly towards said upper surface;

(i) removing a first portion of said bulk liquid phase from said bottom portion of said degassing zone;

(j) pressurizing said first portion of said bulk liquid phase to from about 1 to 50 psig;

(k) discharging said first portion of said bulk liquid phase through said second spray nozzle means so as to form a second spray suspension;

(l) coalescing said second spray suspension into said bulk liquid phase, said second spray suspension being directed towards said upper surface; and (m) removing and separating a second portion of said bulk liquid phase.

* * * * *